(12) United States Patent
Wilson et al.

(10) Patent No.: US 9,210,401 B2
(45) Date of Patent: Dec. 8, 2015

(54) PROJECTED VISUAL CUES FOR GUIDING PHYSICAL MOVEMENT

(75) Inventors: Andrew Wilson, Seattle, WA (US);
Hrvoje Benko, Seattle, WA (US);
Rajinder Sodhi, Champaign, IL (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 13/463,585

(22) Filed: May 3, 2012

(65) Prior Publication Data

US 2013/0295539 A1 Nov. 7, 2013

(51) Int. Cl.

| H04N 13/00 | (2006.01) |
|---|---|
| G09B 19/00 | (2006.01) |
| G06F 3/01 | (2006.01) |
| G06F 19/00 | (2011.01) |
| H04N 9/31 | (2006.01) |
| G06K 9/00 | (2006.01) |
| A63B 69/00 | (2006.01) |

(52) U.S. Cl.
CPC .............. *H04N 13/004* (2013.01); *G06F 3/017* (2013.01); *G06F 19/3481* (2013.01); *G06K 9/00355* (2013.01); *G09B 19/003* (2013.01); *H04N 9/3147* (2013.01); *H04N 9/3185* (2013.01); *A63B 69/004* (2013.01)

(58) Field of Classification Search
CPC ....... A63B 69/00; G09B 19/00; G09B 19/003
USPC .................. 434/247, 248, 249, 250, 251, 252
See application file for complete search history.

(56) References Cited

U.S. PATENT DOCUMENTS

| 4,627,620 A | 12/1986 | Yang |
| 4,630,910 A | 12/1986 | Ross et al. |
| 4,645,458 A | 2/1987 | Williams |
| 4,695,953 A | 9/1987 | Blair et al. |
| 4,702,475 A | 10/1987 | Elstein et al. |
| 4,711,543 A | 12/1987 | Blair et al. |
| 4,751,642 A | 6/1988 | Silva et al. |

(Continued)

FOREIGN PATENT DOCUMENTS

| CN | 201254344 B | 6/2010 | |
| DE | PCT/EP2011/066853 | * 10/2011 | ............. A61B 19/00 |

(Continued)

OTHER PUBLICATIONS

Zhu, et al., "A Bayesian Framework for Human Body Pose Tracking from Depth Image Sequences", Retrieved at <<http://www.mdpi.com/1424-8220/10/5/5280/pdf>>, Sensors 2010, May 25, 2010, pp. 5280-5293.

(Continued)

*Primary Examiner* — Peter Egloff
*Assistant Examiner* — Robert P Bullington
(74) *Attorney, Agent, or Firm* — Aaron Chatterjee; Judy Yee; Micky Minhas

(57) ABSTRACT

Physical movement of a human subject may be guided by a visual cue. A physical environment may be observed to identify a current position of a body portion of the human subject. A model path of travel may be obtained for the body portion of the human subject. The visual cue may be projected onto the human subject and/or into a field of view of the human subject. The visual cue may indicate the model path of travel for the body portion of the human subject.

20 Claims, 4 Drawing Sheets

(56) References Cited

U.S. PATENT DOCUMENTS

| | | |
|---|---|---|
| 4,796,997 A | 1/1989 | Svetkoff et al. |
| 4,809,065 A | 2/1989 | Harris et al. |
| 4,817,950 A | 4/1989 | Goo |
| 4,843,568 A | 6/1989 | Krueger et al. |
| 4,893,183 A | 1/1990 | Nayar |
| 4,901,362 A | 2/1990 | Terzian |
| 4,925,189 A | 5/1990 | Braeunig |
| 5,101,444 A | 3/1992 | Wilson et al. |
| 5,148,154 A | 9/1992 | MacKay et al. |
| 5,184,295 A | 2/1993 | Mann |
| 5,229,754 A | 7/1993 | Aoki et al. |
| 5,229,756 A | 7/1993 | Kosugi et al. |
| 5,239,463 A | 8/1993 | Blair et al. |
| 5,239,464 A | 8/1993 | Blair et al. |
| 5,288,078 A | 2/1994 | Capper et al. |
| 5,295,491 A | 3/1994 | Gevins |
| 5,320,538 A | 6/1994 | Baum |
| 5,347,306 A | 9/1994 | Nitta |
| 5,385,519 A | 1/1995 | Hsu et al. |
| 5,405,152 A | 4/1995 | Katanics et al. |
| 5,417,210 A | 5/1995 | Funda et al. |
| 5,423,554 A | 6/1995 | Davis |
| 5,454,043 A | 9/1995 | Freeman |
| 5,469,740 A | 11/1995 | French et al. |
| 5,495,576 A | 2/1996 | Ritchey |
| 5,516,105 A | 5/1996 | Eisenbrey et al. |
| 5,524,637 A | 6/1996 | Erickson et al. |
| 5,534,917 A | 7/1996 | MacDougall |
| 5,563,988 A | 10/1996 | Maes et al. |
| 5,577,981 A | 11/1996 | Jarvik |
| 5,580,249 A | 12/1996 | Jacobsen et al. |
| 5,594,469 A | 1/1997 | Freeman et al. |
| 5,597,309 A | 1/1997 | Riess |
| 5,616,078 A | 4/1997 | Oh |
| 5,617,312 A | 4/1997 | Iura et al. |
| 5,638,300 A | 6/1997 | Johnson |
| 5,641,288 A | 6/1997 | Zaenglein |
| 5,682,196 A | 10/1997 | Freeman |
| 5,682,229 A | 10/1997 | Wangler |
| 5,690,582 A | 11/1997 | Ulrich et al. |
| 5,703,367 A | 12/1997 | Hashimoto et al. |
| 5,704,837 A | 1/1998 | Iwasaki et al. |
| 5,715,834 A | 2/1998 | Bergamasco et al. |
| 5,875,108 A | 2/1999 | Hoffberg et al. |
| 5,877,803 A | 3/1999 | Wee et al. |
| 5,913,727 A | 6/1999 | Ahdoot |
| 5,933,125 A | 8/1999 | Fernie |
| 5,980,256 A | 11/1999 | Carmein |
| 5,989,157 A | 11/1999 | Walton |
| 5,995,649 A | 11/1999 | Marugame |
| 6,005,548 A | 12/1999 | Latypov et al. |
| 6,009,210 A | 12/1999 | Kang |
| 6,054,991 A | 4/2000 | Crane et al. |
| 6,066,075 A | 5/2000 | Poulton |
| 6,072,494 A | 6/2000 | Nguyen |
| 6,073,489 A | 6/2000 | French et al. |
| 6,077,201 A | 6/2000 | Cheng et al. |
| 6,098,458 A | 8/2000 | French et al. |
| 6,100,896 A | 8/2000 | Strohecker et al. |
| 6,101,289 A | 8/2000 | Kellner |
| 6,128,003 A | 10/2000 | Smith et al. |
| 6,130,677 A | 10/2000 | Kunz |
| 6,141,463 A | 10/2000 | Covell et al. |
| 6,147,678 A | 11/2000 | Kumar et al. |
| 6,152,856 A | 11/2000 | Studor et al. |
| 6,159,100 A | 12/2000 | Smith |
| 6,173,066 B1 | 1/2001 | Peurach et al. |
| 6,181,343 B1 | 1/2001 | Lyons |
| 6,188,777 B1 | 2/2001 | Darrell et al. |
| 6,215,890 B1 | 4/2001 | Matsuo et al. |
| 6,215,898 B1 | 4/2001 | Woodfill et al. |
| 6,226,396 B1 | 5/2001 | Marugame |
| 6,229,913 B1 | 5/2001 | Nayar et al. |
| 6,256,033 B1 | 7/2001 | Nguyen |
| 6,256,400 B1 | 7/2001 | Takata et al. |
| 6,283,860 B1 | 9/2001 | Lyons et al. |
| 6,289,112 B1 | 9/2001 | Jain et al. |
| 6,299,308 B1 | 10/2001 | Voronka et al. |
| 6,308,565 B1 | 10/2001 | French et al. |
| 6,316,934 B1 | 11/2001 | Amorai-Moriya et al. |
| 6,363,160 B1 | 3/2002 | Bradski et al. |
| 6,384,819 B1 | 5/2002 | Hunter |
| 6,411,744 B1 | 6/2002 | Edwards |
| 6,430,997 B1 | 8/2002 | French et al. |
| 6,476,834 B1 | 11/2002 | Doval et al. |
| 6,496,598 B1 | 12/2002 | Harman |
| 6,503,195 B1 | 1/2003 | Keller et al. |
| 6,539,931 B2 | 4/2003 | Trajkovic et al. |
| 6,570,555 B1 | 5/2003 | Prevost et al. |
| 6,633,294 B1 | 10/2003 | Rosenthal et al. |
| 6,640,202 B1 | 10/2003 | Dietz et al. |
| 6,661,918 B1 | 12/2003 | Gordon et al. |
| 6,681,031 B2 | 1/2004 | Cohen et al. |
| 6,714,665 B1 | 3/2004 | Hanna et al. |
| 6,731,799 B1 | 5/2004 | Sun et al. |
| 6,738,066 B1 | 5/2004 | Nguyen |
| 6,765,726 B2 | 7/2004 | French et al. |
| 6,788,809 B1 | 9/2004 | Grzeszczuk et al. |
| 6,801,637 B2 | 10/2004 | Voronka et al. |
| 6,873,723 B1 | 3/2005 | Aucsmith et al. |
| 6,876,496 B2 | 4/2005 | French et al. |
| 6,937,742 B2 | 8/2005 | Roberts et al. |
| 6,950,534 B2 | 9/2005 | Cohen et al. |
| 7,003,134 B1 | 2/2006 | Covell et al. |
| 7,036,094 B1 | 4/2006 | Cohen et al. |
| 7,038,855 B2 | 5/2006 | French et al. |
| 7,039,676 B1 | 5/2006 | Day et al. |
| 7,042,440 B2 | 5/2006 | Pryor et al. |
| 7,050,606 B2 | 5/2006 | Paul et al. |
| 7,058,204 B2 | 6/2006 | Hildreth et al. |
| 7,060,957 B2 | 6/2006 | Lange et al. |
| 7,113,918 B1 | 9/2006 | Ahmad et al. |
| 7,121,946 B2 | 10/2006 | Paul et al. |
| 7,170,492 B2 | 1/2007 | Bell |
| 7,184,048 B2 | 2/2007 | Hunter |
| 7,202,898 B1 | 4/2007 | Braun et al. |
| 7,222,078 B2 | 5/2007 | Abelow |
| 7,227,526 B2 | 6/2007 | Hildreth et al. |
| 7,259,747 B2 | 8/2007 | Bell |
| 7,308,112 B2 | 12/2007 | Fujimura et al. |
| 7,317,836 B2 | 1/2008 | Fujimura et al. |
| 7,348,963 B2 | 3/2008 | Bell |
| 7,359,121 B2 | 4/2008 | French et al. |
| 7,367,887 B2 | 5/2008 | Watabe et al. |
| 7,379,563 B2 | 5/2008 | Shamaie |
| 7,379,566 B2 | 5/2008 | Hildreth |
| 7,389,591 B2 | 6/2008 | Jaiswal et al. |
| 7,412,077 B2 | 8/2008 | Li et al. |
| 7,421,093 B2 | 9/2008 | Hildreth et al. |
| 7,430,312 B2 | 9/2008 | Gu |
| 7,436,496 B2 | 10/2008 | Kawahito |
| 7,450,736 B2 | 11/2008 | Yang et al. |
| 7,452,275 B2 | 11/2008 | Kuraishi |
| 7,460,690 B2 | 12/2008 | Cohen et al. |
| 7,489,812 B2 | 2/2009 | Fox et al. |
| 7,536,032 B2 | 5/2009 | Bell |
| 7,555,142 B2 | 6/2009 | Hildreth et al. |
| 7,560,701 B2 | 7/2009 | Oggier et al. |
| 7,570,805 B2 | 8/2009 | Gu |
| 7,574,020 B2 | 8/2009 | Shamaie |
| 7,576,727 B2 | 8/2009 | Bell |
| 7,590,262 B2 | 9/2009 | Fujimura et al. |
| 7,593,552 B2 | 9/2009 | Higaki et al. |
| 7,598,942 B2 | 10/2009 | Underkoffler et al. |
| 7,607,509 B2 | 10/2009 | Schmiz et al. |
| 7,620,202 B2 | 11/2009 | Fujimura et al. |
| 7,668,340 B2 | 2/2010 | Cohen et al. |
| 7,680,298 B2 | 3/2010 | Roberts et al. |
| 7,683,954 B2 | 3/2010 | Ichikawa et al. |
| 7,684,592 B2 | 3/2010 | Paul et al. |
| 7,701,439 B2 | 4/2010 | Hillis et al. |
| 7,702,130 B2 | 4/2010 | Im et al. |
| 7,704,135 B2 | 4/2010 | Harrison, Jr. |
| 7,710,391 B2 | 5/2010 | Bell et al. |

(56) References Cited

U.S. PATENT DOCUMENTS

| | | | |
|---|---|---|---|
| 7,729,530 | B2 | 6/2010 | Antonov et al. |
| 7,746,345 | B2 | 6/2010 | Hunter |
| 7,760,182 | B2 | 7/2010 | Ahmad et al. |
| 7,809,167 | B2 | 10/2010 | Bell |
| 7,834,846 | B1 | 11/2010 | Bell |
| 7,852,262 | B2 | 12/2010 | Namineni et al. |
| RE42,256 | E | 3/2011 | Edwards |
| 7,898,522 | B2 | 3/2011 | Hildreth et al. |
| 8,035,612 | B2 | 10/2011 | Bell et al. |
| 8,035,614 | B2 | 10/2011 | Bell et al. |
| 8,035,624 | B2 | 10/2011 | Bell et al. |
| 8,072,470 | B2 | 12/2011 | Marks |
| 2005/0159759 | A1* | 7/2005 | Harbaugh et al. ............ 606/130 |
| 2007/0253614 | A1* | 11/2007 | Jung et al. .................... 382/131 |
| 2008/0026838 | A1 | 1/2008 | Dunstan et al. |
| 2009/0298650 | A1 | 12/2009 | Kutliroff |
| 2010/0277411 | A1 | 11/2010 | Yee et al. |
| 2010/0306685 | A1 | 12/2010 | Giaimo, III et al. |
| 2012/0206577 | A1* | 8/2012 | Guckenberger et al. ........ 348/47 |

FOREIGN PATENT DOCUMENTS

| | | | |
|---|---|---|---|
| EP | 0583061 | A2 | 2/1994 |
| JP | 08044490 | A1 | 2/1996 |
| WO | 93/10708 | A1 | 6/1993 |
| WO | 97/17598 | A1 | 5/1997 |
| WO | 99/44698 | A1 | 9/1999 |

OTHER PUBLICATIONS

Skeels, et al., "ShapeShift: A Projector-Guided Sculpture System", Retrieved at <<http://www.acm.org/uist/archive/adjunct/2007/pdf/posters/p67-skeels.pdf>>, 20th ACM Symposium on User Interface Software and Technology, Oct. 10, 2007, pp. 2.

Bedwell, et al., "Pervasive Projection: Exploring the Potential of Mobile Phone Projectors", Retrieved at <<http://eis.comp.lancs.ac.uk/workshops/ubiproject2010/pdf/bedwell_ubiprojection2010.pdf>>, 8th International Conference on Pervasive Computing, May 17-21, 2010, pp. 4.

Wilson, et al., "Combining Multiple Depth Cameras and Projectors for Interactions On, Above, and Between Surfaces", Retrieved at <<http://research.microsoft.com/en-us/um/people/awilson/publications/wilsonuist2010/wilson%20uist%202010%20lightspace.pdf>>, Proceedings of the 23nd annual ACM symposium on User interface software and technology, Oct. 3-6, 2010, pp. 10.

Gröhn, et al., "3D Visualization of Building Services in Virtual Environment", Retrieved at <<http://www.tkk.fi/events/ecaade/E2001presentations/18_01_grohn.pdf, SPIE Proceedings, vol. 4297, Jun. 22, 2001, pp. 523-528.

Kanade et al., "A Stereo Machine for Video-rate Dense Depth Mapping and Its New Applications", IEEE Computer Society Conference on Computer Vision and Pattern Recognition, 1996, pp. 196-202,The Robotics Institute, Carnegie Mellon University, Pittsburgh, PA.

Miyagawa et al., "CCD-Based Range Finding Sensor", Oct. 1997, pp. 1648-1652, vol. 44 No. 10, IEEE Transactions on Electron Devices.

Rosenhahn et al., "Automatic Human Model Generation", 2005, pp. 41-48, University of Auckland (CITR), New Zealand.

Aggarwal et al., "Human Motion Analysis: A Review", IEEE Nonrigid and Articulated Motion Workshop, 1997, University of Texas at Austin, Austin, TX.

Shao et al., "An Open System Architecture for a Multimedia and Multimodal User Interface", Aug. 24, 1998, Japanese Society for Rehabilitation of Persons with Disabilities (JSRPD), Japan.

Kohler, "Special Topics of Gesture Recognition Applied in Intelligent Home Environments", In Proceedings of the Gesture Workshop, 1998, pp. 285-296, Germany.

Kohler, "Vision Based Remote Control in Intelligent Home Environments", University of Erlangen-Nuremberg/Germany, 1996, pp. 147-154, Germany.

Kohler, "Technical Details and Ergonomical Aspects of Gesture Recognition applied in Intelligent Home Environments", 1997, Germany.

Hasegawa et al., "Human-Scale Haptic Interaction with a Reactive Virtual Human in a Real-Time Physics Simulator", Jul. 2006, vol. 4, No. 3, Article 6C, ACM Computers in Entertainment, New York, NY.

Qian et al., "A Gesture-Driven Multimodal Interactive Dance System", Jun. 2004, pp. 1579-1582, IEEE International Conference on Multimedia and Expo (ICME), Taipei, Taiwan.

Zhao, "Dressed Human Modeling, Detection, and Parts Localization", 2001, The Robotics Institute, Carnegie Mellon University, Pittsburgh, PA.

He, "Generation of Human Body Models", Apr. 2005, University of Auckland, New Zealand.

Isard et al., "Condensation—Conditional Density Propagation for Visual Tracking", 1998, pp. 5-28, International Journal of Computer Vision 29(1), Netherlands.

Livingston, "Vision-based Tracking with Dynamic Structured Light for Video See-through Augmented Reality", 1998, University of North Carolina at Chapel Hill, North Carolina, USA.

Wren et al., "Pfinder: Real-Time Tracking of the Human Body", MIT Media Laboratory Perceptual Computing Section Technical Report No. 353, Jul. 1997, vol. 19, No. 7, pp. 780-785, IEEE Transactions on Pattern Analysis and Machine Intelligence, Caimbridge, MA.

Breen et al., "Interactive Occlusion and Collusion of Real and Virtual Objects in Augmented Reality", Technical Report ECRC-95-02, 1995, European Computer-Industry Research Center GmbH, Munich, Germany.

Freeman et al., "Television Control by Hand Gestures", Dec. 1994, Mitsubishi Electric Research Laboratories, TR94-24, Caimbridge, MA.

Hongo et al., "Focus of Attention for Face and Hand Gesture Recognition Using Multiple Cameras", Mar. 2000, pp. 156-161, 4th IEEE International Conference on Automatic Face and Gesture Recognition, Grenoble, France.

Pavlovic et al., "Visual Interpretation of Hand Gestures for Human-Computer Interaction: A Review", Jul. 1997, pp. 677-695, vol. 19, No. 7, IEEE Transactions on Pattern Analysis and Machine Intelligence.

Azarbayejani et al., "Visually Controlled Graphics", Jun. 1993, vol. 15, No. 6, IEEE Transactions on Pattern Analysis and Machine Intelligence.

Granieri et al., "Simulating Humans in VR", The British Computer Society, Oct. 1994, Academic Press.

Brogan et al., "Dynamically Simulated Characters in Virtual Environments", Sep./Oct. 1998, pp. 2-13, vol. 18, Issue 5, IEEE Computer Graphics and Applications.

Fisher et al., "Virtual Environment Display System", ACM Workshop on Interactive 3D Graphics, Oct. 1986, Chapel Hill, NC.

"Virtual High Anxiety", Tech Update, Aug. 1995, pp. 22.

Sheridan et al., "Virtual Reality Check", Technology Review, Oct. 1993, pp. 22-28, vol. 96, No. 7.

Stevens, "Flights into Virtual Reality Treating Real World Disorders", The Washington Post, Mar. 27, 1995, Science Psychology, 2 pages.

"Simulation and Training", 1994, Division Incorporated.

* cited by examiner

PROJECTED VISUAL CUES FOR GUIDING PHYSICAL MOVEMENT

BACKGROUND

Optical sensor systems may be used to identify objects within a physical environment and to track those objects as they move throughout the physical environment. Optical tracking of a human subject may be used to control an electronic device such as a computer or a gaming device. As one such example, a human subject may provide a control input to an electronic device by moving his or her body within a scene observed by one or more optical sensors.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Physical movement of a human subject may be guided by a visual cue. A physical environment is observed to identify a current position of a body portion of the human subject. A model path of travel is obtained for the body portion of the human subject. A visual cue that indicates the model path of travel for the body portion is projected onto the human subject and/or into a field of view of the human subject.

DETAILED DESCRIPTION

A visual cue may be projected onto a human subject and/or into a field of view of the human subject to guide physical movement. The visual cue may enable a human subject to achieve greater accuracy or improved technique with respect to the physical movement than may otherwise be achieved without the visual cue. Physical movements that are guided by the visual cue may be applicable to controlling an electronic device, performing a physical exercise or task, engaging in a form of physical therapy, or other suitable endeavor.

The use of visual cues for guiding physical movement has virtually limitless applications. For example, a novice musician learning to play an instrument may be directed to a correct posture by a visual cue when their form begins to drift. An amateur athlete working on punching exercises during martial arts training may be guided toward the proper form or style by a visual cue. Physical therapy patients recovering from an injury may be guided through their exercises by a visual cue.

Figure 1:
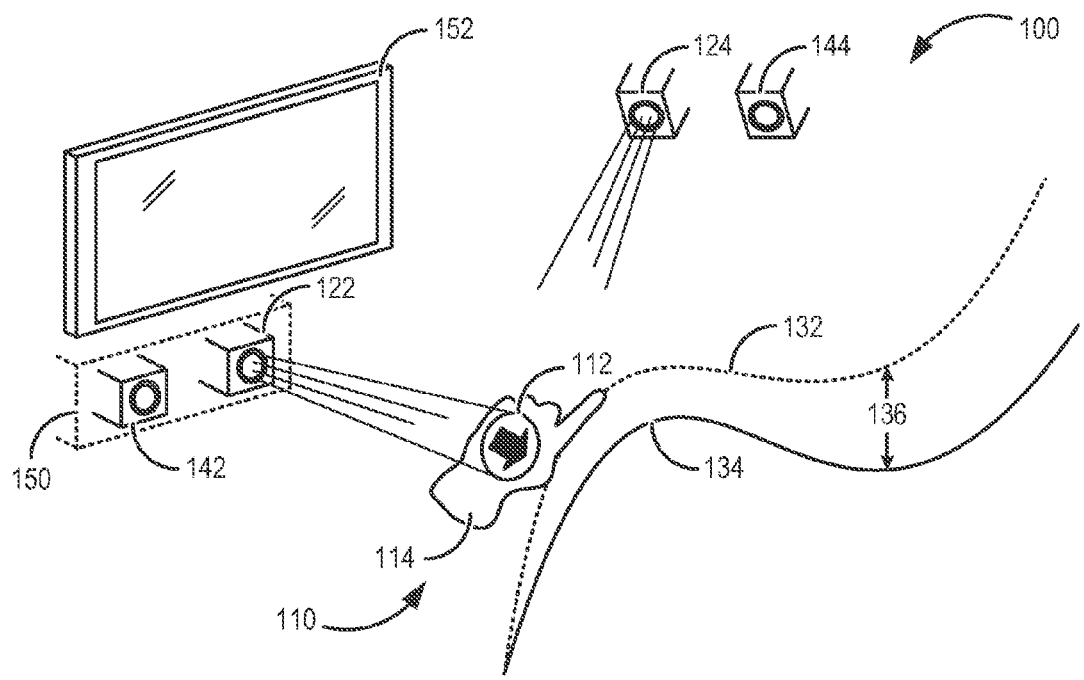
FIG. 1 shows an example use-environment.

FIG. 1 shows an example use-environment 100 in which physical movement of a human subject 110 is guided by a visual cue 112 that is projected by one or more image projectors 122 and/or 124. In FIG. 1, visual cue 112 is projected onto body portion 114 (e.g., a hand) of the human subject. However, a visual cue may be alternatively or additionally projected onto a different body portion of the human subject and/or may be projected into a field of view of the human subject. The use of multiple image projectors may reduce the effects of occlusion of one or more of the light paths that may occur as the human subject moves within the physical environment. While FIG. 1 illustrates a single human subject, visual cues may be projected for two or more different subjects without departing from the scope of this disclosure.

Visual cue 112 may be used to guide the body portion of the human subject toward or along model path of travel 134. For example, visual cue 112 may include a directional indicator (e.g., an arrow) that guides the body portion toward model path of travel 134. It will be understood that visual cue 112 is merely one non-limiting example of a visual cue, as other types of visual cues may be used. Physical movement of body portion 114 along a path of travel 132 may, at times, deviate from a model path of travel 134 as indicated by example deviation 136.

In FIG. 1, the position of body portion 114 and/or other body portions of the human subject may be identified by observing the physical environment. As a nonlimiting example, the physical environment may be imaged via one or more optical sensors, such as optical sensors 142 and/or 144. In at least some implementations, one or more optical sensors and/or one or more image projectors may be contained within or may form part of a common device. For example, in FIG. 1, image projector 122 and optical sensor 142 form part of a common peripheral device 150. Peripheral device 150 may be operatively connected to one or more other electronic devices, such as a computer, gaming device, or other suitable device. It will be understood that optical imaging need not be used in all embodiments. In some embodiments, observation of the physical environment may be performed electromagnetically, via inertial measurements (e.g., using worn trackers), or using other suitable approaches.

Within use-environment 100, visual information may be presented to the human subject via a graphical display 152. Peripheral device 150 may reside, for example, at a location that is near graphical display 152. However, in at least some implementations, one or more optical sensors and/or one or more image projectors may reside at a different location from one or more other optical sensors and/or image projectors. For example, in FIG. 1, image projector 124 and optical sensor 144 are located above (e.g., overhead of) the human subject. It will be understood that any suitable number of image projectors and/or optical sensors may be located at any suitable location relative to a human subject.

In at least some implementations, one or more optical sensors and/or one or more image projectors may reside at or form part of a device that is worn by or held by the human subject. As one example, an optical sensor and/or an image projector may be integrated into a pair of glasses that are worn by the human subject. As another example, an optical sensor and/or image projector may be integrated into a hand-held mobile device.

In at least some implementation, the head of a human subject can be tracked, and the shape of the visual cue can be augmented in accordance with the orientation of the head. For example, if the user changes head position, a 3D arrow visual cue pointing upwards can be augmented to take into account the new head position to create the correct perspective view (e.g., the 3D arrow is adjusted such that it always looks like it is pointed upwards regardless of the position of the human subject's head).

Figure 2:
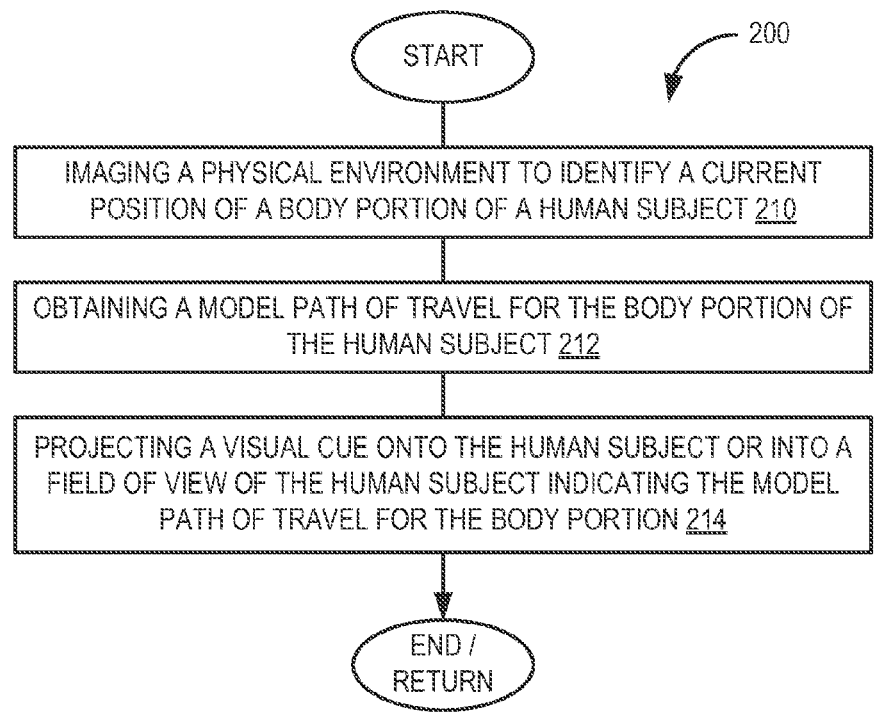
FIG. 2 shows a flow diagram depicting an example method for guiding physical movement of a human subject.

FIG. 2 shows a flow diagram depicting an example method 200 for guiding physical movement of a human subject. While method 200 describes techniques for guiding an individual body portion, it will be understood that method 200 may be used to independently guide multiple body portions of one or more human subjects along independent model paths of travel. Method 200 may be implemented within the context of previously described use-environment 100. However, it will be understood that use-environment 100 is merely a non-limiting example of a context in which method 200 may be implemented.

At 210, the method may include imaging or otherwise observing a physical environment to identify a current position of one or more body portions of a human subject. Any suitable observation technique may be used to identify the current position of the human subject or the subject's one or more body portions that are present within an imaged scene. As a non-limiting example, a physical environment may be imaged via one or more optical sensors that include a depth camera to identify a three-dimensional position (e.g., x position, y position, and z position) of objects within the imaged scene. Further aspects of these and other imaging techniques will be described in greater detail with reference to FIG. 10.

Observing a physical environment may be performed over a period of time to capture transient aspects of physical objects. For example, a current position of one or more body portions of a human subject may be updated over time as those body portions move within the physical environment. A change in position of a body portion that occurs between two or more instances in time may define a path of travel for that body portion in one, two, or three-dimensional space.

At 212, the method may include obtaining a model path of travel for the body portion of the human subject. A model path of travel may be obtained by programmatically generating the model path of travel or by receiving a pre-defined model path of travel from a data source. As one example, the data source may include or may be defined by an application program that includes one or more pre-defined model paths of travel. As another example, a human subject may record or otherwise define a model path of travel by moving within an observed scene.

A model path of travel may be defined by a series of two or more points in dimensional space with each point represented by one or more coordinate values (e.g., x, y, and z coordinate values) defining the location of that point. In at least some implementations, each point may be associated with an order value that indicates a relative order of that point within the series of points. The order value may indicate a time value for each of the one or more points, for example, if the model path of travel defines a timing of movement along the model path of travel. As another example, a relative order of points defining a model path of travel may be indicated by segments that link two respective points of the series. As yet another example, a relative order of points defining a model path of travel may be indicated by their respective order within a list of points.

A model path of travel may be a one-dimensional or multi-dimensional model path of travel. A one-dimensional model path of travel includes one spatial dimension that defines motion along a straight line. A multi-dimensional model path of travel may include: two spatial dimensions that defines motion along a non-straight line within a plane; three spatial dimensions that defines motion along a non-straight line in multiple planes; a time dimension and one spatial dimension; or a time dimension and two or more spatial dimensions. Examples of higher-order spatial dimensions may include twisting or rotation of body portions of the human subject that may form part of a model path of travel in addition to or as an alternative to translation of the body portion.

If the model path of travel does not include a time dimension, a timing of movement of a body portion along the model path of travel may be at the discretion of the human subject. If the model path of travel includes a time dimension, the timing of movement of the body portion along the model path of travel may be defined, at least in part, by the time dimension of that model path of travel, including respective time values associated with points along that model path of travel. In such case, the human subject may be guided along the model path of travel in accordance with the time dimension, and may be provided visual cues to indicate a relationship between the current position of the body portion and a model position along the model path of travel that accords with the time values of the time dimension.

At 214, the method may include projecting a visual cue onto the human subject. The visual cue may indicate the model path of travel for the body portion of the human subject. For example, the visual cue may be projected onto the body portion of the human subject or onto a different body portion of the human subject.

By projecting the visual cue onto the body portion that is being guided, the human subject may obtain visual feedback (e.g., where a user has already moved) and/or feedforward (e.g., where a user is to move next) information relating to the model path of travel while that human subject is observing that body portion. Accordingly, the human subject is able to focus on the body portion rather than dividing attention between the body portion and a dedicated graphical display device. Furthermore, projection of the visual cue onto the human subject or into a field of view of the human subject enables the human subject to face away from a dedicated graphical display device.

If two or more image projectors are available for projecting the visual cue, one, some, or all of those image projectors may be used to project the visual cue. In at least some implementations, the physical environment that was imaged at 210 may be used to identify which image projectors are able to project the visual cue onto a target object (e.g., a surface of the human subject or other object) without occlusion of that projection by another object within the physical environment. Image projectors that are unable to project the visual cue onto the target object without occlusion may not be used to project the visual cue, at least temporarily or until occlusion has abated. Image projectors that are able to project the visual cue onto the target object may be used to project the visual cue.

In at least some implementations, a spatial parameter (e.g., location and/or depth) of projection of the visual cue may be varied as a body portion moves within the physical environment to maintain projection of the visual cue within a boundary of the body portion. This technique may be referred to as a self-guided implementation in which the visual cue tracks the body portion of the human subject as identified from the imaged environment. In this context, the human subject may choose the pace at which the body portion follows the visual cues. Aspects of object tracking will be described in greater detail with reference to FIG. 10.

In another implementation, the visual cue may instead follow the model path of travel or track a model position along the model path of travel. This technique may be referred to as a system imposed timing implementation of the visual cue in which the human subject attempts to follow the projected visual cue within the physical environment. Hence, under the system imposed timing implementation, the visual cue may not be projected onto the body portion at all times, for example, if the body portion is not located at a model position along the model path of travel. However, in other examples, the visual cue may be maintained on or within the boundaries of the body portion even if the human subject deviates from the model path or model position along the model path. As one example, to ensure that visual cues are not projected outside the boundary of the body portion, a derivative map of a depth image of the body portion may be computed to check for threshold changes in depth at the boundaries of the body portion. If a visual cue reaches a contour or boundary of the body portion, the visual cue may be stopped from moving or slowed along the model path of travel until the human subject has caught up to the visual cue.

Alternatively or additionally, the visual cue may be projected into a field of view of the human subject. In at least some implementations, the field of view of the human subject may be identified by observing the physical environment as previously described at 210. For example, a field of view of a human subject may be identified or inferred from an orientation of the head of the human subject and/or the location of physical objects (e.g., walls, body portions, furniture, or other suitable surfaces) within the physical environment upon which the visual cue may be projected.

The visual cue may indicate the model path of travel by showing how the human subject's previous physical movements tracked the model path of travel. This type of visual cue may be used to provide visual feedback information to the human subject. Alternatively or additionally, the visual cue may indicate the model path of travel by showing how the human subject's future physical movements can mimic the model path of travel. This type of visual cue may be used to provide visual feedforward information to the human subject.

In at least some implementations, the visual cue may indicate the model path of travel by showing a deviation between a current position of the body portion and a model position along the model path of travel. For example, the method may further include determining a magnitude and/or a direction of the deviation between a current position of the body portion and a model position along the model path of travel. The visual cue may indicate the magnitude and/or the direction of the deviation. As will be described in greater detail with reference to FIGS. 7, 8, and 9, a variety of different approaches may be used to guide a human subject toward or along a model path of travel using a visual cue.

Figure 3:
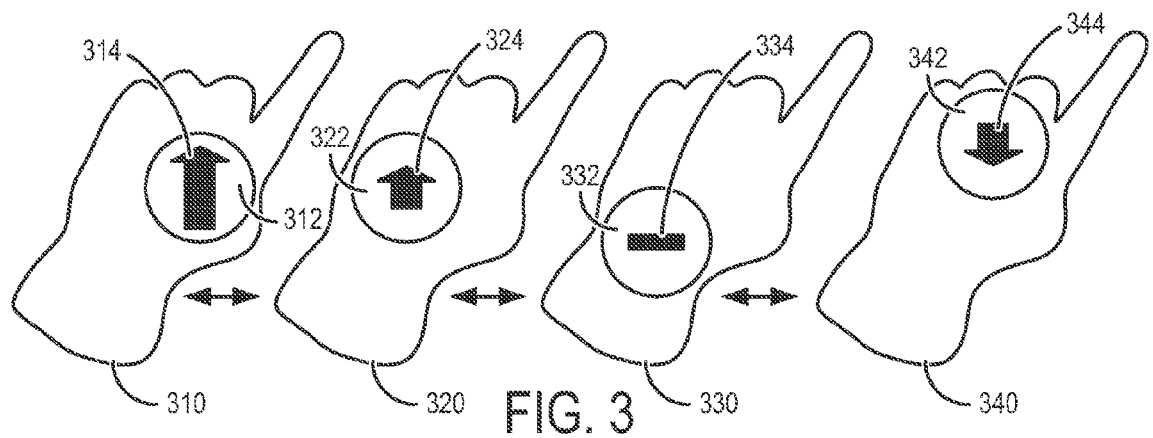
FIG. 3 shows a series of visual cues that may be used to guide physical movement of a human subject.

A visual cue may take a variety of different forms to provide feedback and/or feedforward information to a human subject. FIG. 3 shows a series of visual cues that may be used to guide physical movement of a human subject. In FIG. 3, a visual cue 312 is projected onto a body portion (e.g., a hand) at 310. In FIG. 3, visual cue 312 takes the form of a visible light portion having circular shape (e.g., a spot). However, it will be understood that a visual cue may include any suitable shape, icon, or form of graphical information.

Visual cue 312 may be used in the context in which a human subject follows the visual cue along the model path of travel. The relative location at which the visual cue is projected within the boundaries of the body portion or other suitable object may indicate a direction (e.g., within a first plane) that the body portion should be moved to follow the model path of travel. In the illustrated example, the visual cues are projected on a hand such that if the user moves his hand so as to center the visual cue on his hand, his hand will follow the model path of travel.

For example, visual cue 312 is projected onto a right side of the body portion at 310, indicating that the body portion should be moved to the right in a horizontal plane. At another instance, visual cue 322 is projected onto a left side of the body portion at 320, indicating that the body portion should be moved to the right in the horizontal plane. At another instance, visual cue 332 is projected onto a near side of the body portion at 330, indicating that the body portion should be moved backward or toward the human subject in the horizontal plane. At yet another instance, visual cue 342 is projected onto a far side of the body portion at 340, indicating that the body portion should be moved forward or away from the human subject in the horizontal plane.

A visual cue may indicate a model path of travel in a higher level of dimensionality by the inclusion of other graphical information. As a non-limiting example, visual cue 312 includes a directional indicator 314 (e.g., an arrow) that directs the human subject to move the body portion in a vertical direction or vertical plane that is perpendicular to the horizontal plane (e.g. in an upward direction relative to the horizontal plane). The directional indicator may be orientated to point along the model path of travel or may indicate a travel path guiding the body portion toward a model position along the model path of travel in a coordinate axis or plane associated with the directional indicator.

Visual cue 322 includes another directional indicator 324 (e.g., an arrow) that is smaller than directional indicator 314. A size (e.g., a length and/or width) of the directional indicator may be used to indicate a magnitude of a deviation between a current position of the body portion and a model position along a model path of travel, at least within the coordinate axis or plane associated with the directional indicator. For example, directional indicator 314 may indicate a greater deviation from the model position than directional indicator 324.

Visual cue 332 includes an icon 334 that may indicate that the current position of the body portion is located along the model path of travel or at a model position along the model path of travel in a coordinate axis or plane associated with the directional indicator. For example, icon 334 may indicate that the body portion is at the correct height relative to the horizontal plane as defined by the model path of travel.

Visual cue 342 includes yet another directional indicator 344 (e.g., an arrow) that is oriented in a different direction than directional indicators 314 and 324. Directional indicator 344 may be used to inform the human subject that the body portion should be moved in a different direction than indicated by directional indicators 314 and 324. For example, directional indicator 344 may indicate that the body portion is to be moved downward relative to the horizontal plane.

While the example directional indicators of FIG. 3 indicate linear paths of travel, it will be appreciated that other directional indicators may be used, including directional indicators that indicate rotation or curved paths of travel (e.g., a clock-wise or counter-clockwise arrow) or other suitable paths of travel.

A visual cue may alternatively or additionally include one or more colors that indicate a relative position of the body portion relative to the model path of travel. The term "color" as used herein may include reference to one or more of the properties of a color, including: hue, colorfulness, chroma, saturation, lightness, and brightness. Accordingly, where a visual cue includes a color, that visual cue may have a different hue, colorfulness, chroma, saturation, lightness, and/or brightness than the surrounding environment and/or other aspects of that visual cue.

Figure 4:
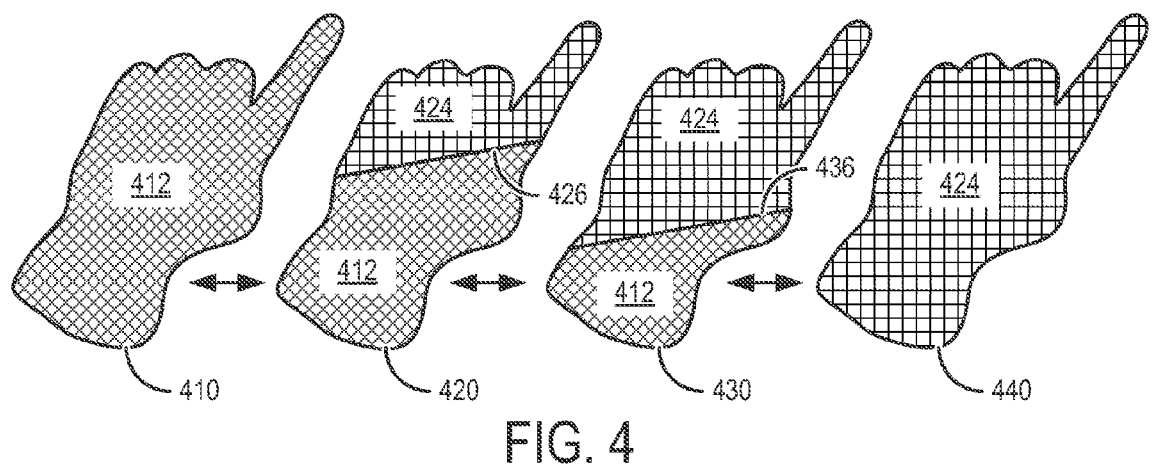
FIG. 4 shows another series of visual cues that may be used to guide physical movement of a human subject.

FIG. 4 shows another series of visual cues that may be used to guide physical movement of a human subject. A visual cue 410 projected onto a hand of a human subject may include a first color 412 (e.g., blue). First color 412 may indicate that the body portion has deviated from a model position and may indicate a relative direction of the deviation. For example, a visual cue 420 projected onto the hand of the human subject may include the first color 412 and a second color 424 (e.g., red) separated by a boundary 426. Boundary 426 may be orientated along the model path of travel in some examples. For example, first color 412 may indicate a deviation from the model path of travel in first direction and second color 424 may indicate a deviation from the model path of travel in a second direction. As another example, first color 412 may indicate that the body portion is at a model position or within a model region along the model path of travel, and second color 424 may indicate a deviation from the model position or model region. Visual cue 430 shows how boundary 436 may be moved relative to boundary 426, for example, as the hand of the human subject deviates from the model path of travel in a direction indicated by second color 424. As the hand continues to deviate in that direction, visual cue 440 further indicates second color 424.

Figure 5:
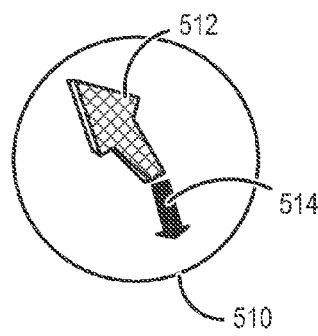
FIG. 5 shows an example visual cue taking the form of a three-dimensional arrow.

A visual cue may include a visual representation of a multi-dimensional directional indicator to guide physical movement of the human subject in multi-dimensional space. FIG. 5 shows an example visual cue 510 taking the form of a three-dimensional arrow 512. Visual cue 510 further includes a virtual shadow 514 for three-dimensional arrow 512. Three-dimensional arrow 512 may be oriented to point along the model path of travel or toward a model position along the model path of travel.

Figure 6:
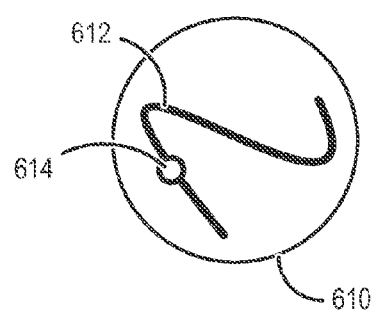
FIG. 6 shows another example visual cue taking the form of a visual representation of a model path of travel.

A visual cue may alternatively or additionally include a visual representation of the model path of travel and/or a current position of the body portion relative to the model path of travel. FIG. 6 shows another example visual cue 610 taking the form of a visual representation of a model path of travel 612. Visual cue 610 further includes a current position 614 of the body portion relative to the model path of travel.

The visual representation of the model path of travel 612 may take the form of a one, two, or three-dimensional model path of travel depending on the dimensionality of that model path. For example, if the model path of travel includes multiple spatial dimensions, the visual cue may include a visual representation of the multi-dimensional model path of travel. As another example, if the model path of travel includes a time dimension, the visual cue may indicate a deviation between the current position and a model position along the model path of travel. The model position may include a time-dependent model position that is registered to a time value associated with a point along the model path. The time value may be measured relative to a time that the movement along the model path of travel was initiated. In at least some implementations, visual cue 610 may further include a visual representation of a model position along model path of travel 612.

The various visual cues described herein may be used alone or in combination to provide an indication of past, current, and/or future position of a body portion. As one example, a visual cue may include a visible light portion that indicates a first direction of movement for the body portion toward or along the model path of travel in a first plane, and a directional indicator that indicates a second direction of movement for the body portion toward or along the model path of travel in a second direction or plane that is perpendicular to the first plane. As another example, the icon-based visual cues of FIG. 3 or 5 may be overlaid on or may incorporate the color-based visual cues of FIG. 4 to indicate a direction of movement in two or more perpendicular planes.

Figure 7:
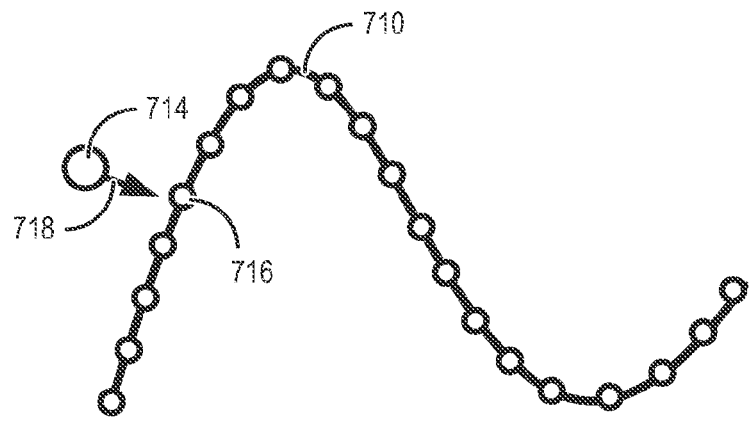
FIG. 7 shows a first example approach for guiding a human subject toward or along a model path of travel.

A visual cue may direct the body portion of the human subject toward or along the model path of travel using a number of different approaches. FIG. 7 shows a first example approach (e.g., referred to as the absolute approach) for guiding a human subject toward or along a model path of travel. As depicted in FIG. 7, a body portion located at a current position 714 is directed toward a nearest model position 716 of model path of travel 710 by a directional indicator 718.

Figure 8:
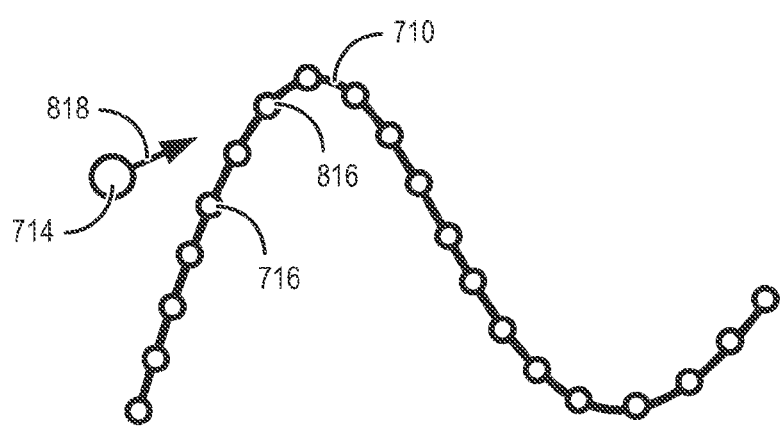
FIG. 8 shows a second example approach for guiding a human subject toward or along a model path of travel.

FIG. 8 shows a second example approach (e.g., referred to as the relaxed absolute approach) for guiding a human subject toward or along a model path of travel. As depicted in FIG. 8, the body portion located at the current position 714 is instead directed toward a future model position 816 of model path of travel 710 by directional indicator 818. Future model position 816 is located further along model path of travel 710 than current model position 716. Accordingly, the human subject is guided back to the model path of travel in a more gradual manner in FIG. 8 than in FIG. 7.

Figure 9:
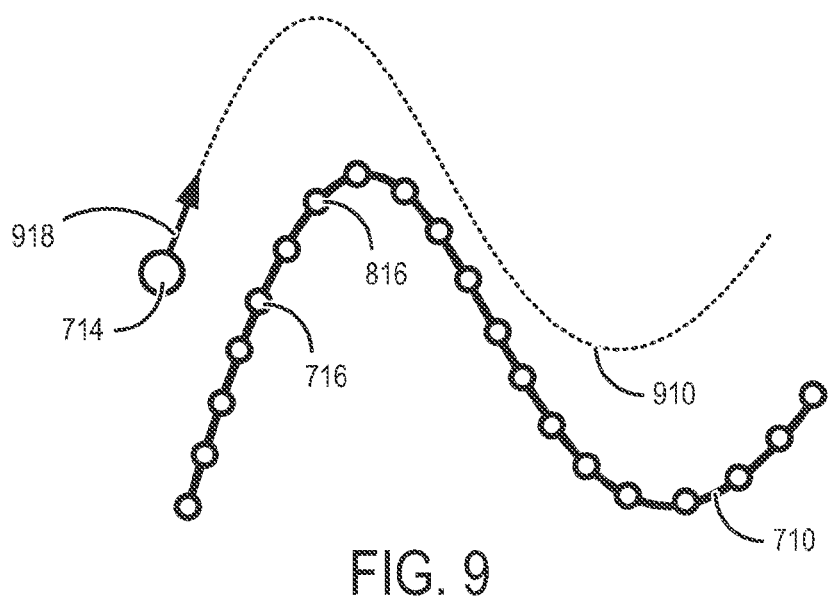
FIG. 9 shows a third example approach for guiding a human subject toward or along a model path of travel.

FIG. 9 shows a third example approach (e.g., referred to as the relative approach) for guiding a human subject toward or along a model path of travel. As depicted in FIG. 9, the body portion located at current position 714 is instead directed by directional indicator 918 along a parallel model path of travel 910 that is offset from model path of travel 710. The approach depicted in FIG. 9 favors relative adherence to the model path of travel rather than absolute adherence to the individual points defining the model path of travel.

Selection of one of the approaches discussed in FIGS. 7, 8, and 9 may be based, at least in part, on the task associated with the physical movement. For example, a dancing movement may be less stringent about following an exact model path, and may therefore utilize a parallel model path of travel that is offset from the model path of travel. Hence, under some scenarios the relative approach of FIG. 9 may be more appropriate. In contrast, some exercises may cause strain or injury to the human subject if physical movement deviates from the model path of travel. Hence, under some scenarios the absolute or relaxed-absolute approaches of FIGS. 7 and 8 may be more appropriate.

In some embodiments, the above described methods and processes may be tied to a computing system including one or more computers and/or peripheral devices. In particular, the methods and processes described herein may be implemented as a computer application, computer service, computer application programming interface (API), computer library, and/or other computer program product.

Figure 10:
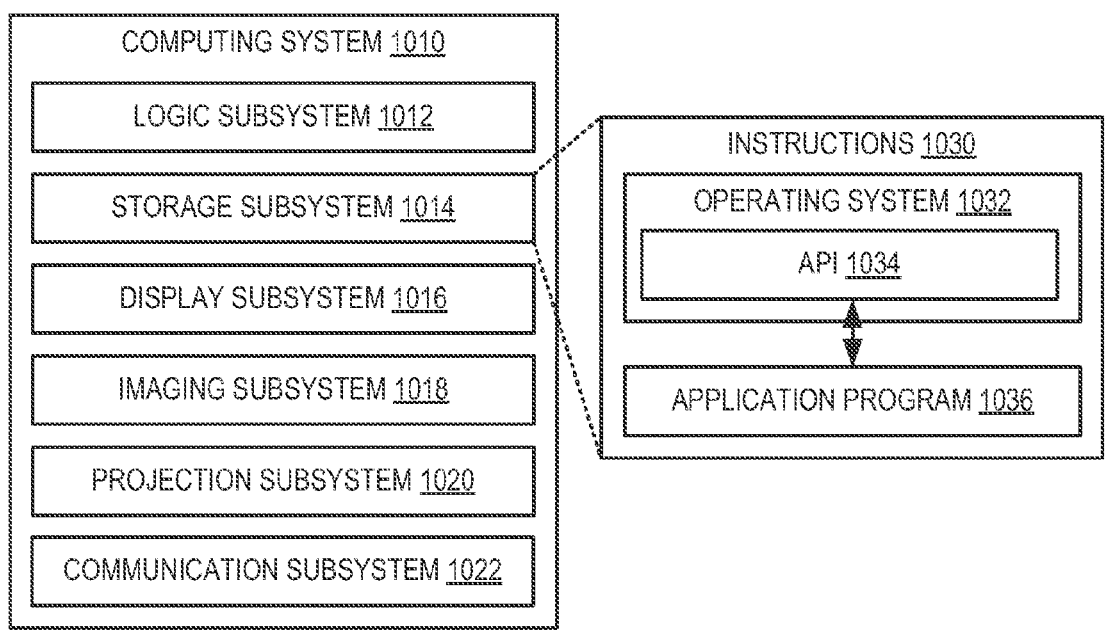
FIG. 10 shows an example computing system.

FIG. 10 schematically shows a non-limiting example of a computing system 1010 that may perform one or more of the above described methods and/or processes. Computing system 1010 is shown in simplified form. It is to be understood that virtually any computer architecture may be used without departing from the scope of this disclosure. In different embodiments, computing system 1010 may take the form of a mainframe computer, server computer, desktop computer, laptop computer, tablet computer, home entertainment computer, network computing device, mobile computing device, mobile communication device, gaming device, etc.

Computing system 1010 includes a logic subsystem 1012 and a storage subsystem 1014. Computing system 1010 may optionally include a display subsystem 1016, imaging subsystem 1018, projection subsystem 1020, communication subsystem 1022, and/or other components not shown in FIG.

10. Computing system 1010 may also optionally include user input devices such as keyboards, mice, game controllers, cameras, microphones, and/or touch screens, for example.

Logic subsystem 1012 may include one or more physical devices configured to execute one or more instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Storage subsystem 1014 may include one or more physical, non-transitory, devices configured to hold data and/or instructions executable by the logic subsystem to implement the herein described methods and processes. When such methods and processes are implemented, the state of storage subsystem 1014 may be transformed (e.g., to hold different data).

Storage subsystem 1014 may include removable media and/or built-in devices. Storage subsystem 1014 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Storage subsystem 1014 may include devices with one or more of the following characteristics: volatile, nonvolatile, dynamic, static, read/write, read-only, random access, sequential access, location addressable, file addressable, and content addressable. In some embodiments, logic subsystem 1012 and storage subsystem 1014 may be integrated into one or more common devices, such as an application specific integrated circuit or a system on a chip.

It is to be appreciated that storage subsystem 1014 includes one or more physical, non-transitory devices. In contrast, in some embodiments aspects of the instructions described herein may be propagated in a transitory fashion by a pure signal (e.g., an electromagnetic signal, an optical signal, etc.) that is not held by a physical device for at least a finite duration. Furthermore, data and/or other forms of information pertaining to the present disclosure may be propagated by a pure signal.

The terms "module," "program," and "engine" may be used to describe an aspect of computing system 1010 that is implemented to perform one or more particular functions. In some cases, such a module, program, or engine may be instantiated via logic subsystem 1012 executing instructions held by storage subsystem 1014. It is to be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" are meant to encompass individual or groups of executable files, data files, libraries, drivers, scripts, database records, etc.

When included, display subsystem 1016 may be used to present a visual representation of data held by storage subsystem 1014. As the herein described methods and processes change the data held by the storage subsystem, and thus transform the state of the storage subsystem, the state of display subsystem 1016 may likewise be transformed to visually represent changes in the underlying data. Display subsystem 1016 may include one or more display devices utilizing virtually any type of technology. Such display devices may be combined with logic subsystem 1012 and/or storage subsystem 1014 in a shared enclosure, or such display devices may be peripheral display devices.

Imaging subsystem 1018 may include one or more optical sensors. One or more of the optical sensors of imaging subsystem 1018 may include or take the form of a depth camera. The depth camera may be capable of observing a scene of a physical environment that includes one or more human subjects, and other physical objects. The depth camera may be used to identify, monitor, or track the human subjects. Virtually any depth finding technology may be used without departing from the scope of this disclosure. Non-limiting examples of depth cameras include time of flight depth cameras and structured light depth cameras. Imaging subsystem 1018 may be combined with one or more of logic subsystem 1012, storage subsystem 1014, and/or projection subsystem 1020 in a shared enclosure. As one example, imaging subsystem 1018 and projection subsystem 1020 may be combined in a shared enclosure that takes the form of a peripheral device. In another example, imaging subsystem 1018 may reside at a separate peripheral device from one or more of logic subsystem 1012, storage subsystem 1014, and/or projection subsystem 1020.

Projection subsystem 1020 may include one or more image projectors. Such image projectors may be capable of projecting visible light onto a physical object. Projection subsystem 1020 may be used to present a visual representation of data held by storage subsystem 1014. As the herein described methods and processes change the data held by the storage subsystem, and thus transform the state of the storage subsystem, the state of projection subsystem 1020 may likewise be transformed to visually represent changes in the underlying data. Virtually any image projector technology may be used without departing from the scope of this disclosure. Projection subsystem 1020 may be combined with one or more of logic subsystem 1012, storage subsystem 1014, and/ or projection subsystem 1020 in a shared enclosure. In another example, projection subsystem 1020 may reside at a separate peripheral device from one or more of logic subsystem 1012, storage subsystem 1014, and/or imaging subsystem 1018.

In at least some implementations, one or more optical sensors of imaging subsystem 1018 and one or more image projectors of projection subsystem 1020 may be located at a known or predetermined distance and/or orientation relative to each other, enabling unification of the image projectors and optical sensors in the same coordinate space. For example, an image projector may be calibrated to a depth camera. Intrinsic parameters of an image projector may be modeled using a diagonal field of view and the center of projection. Extrinsic parameters of an image projector may be computed from non-coplanar correspondence between points that are within both the projection area of the image projector and the scene imaged by the depth camera. Once correspondence is established between two-dimensional points of the image projector and three-dimensional points of the depth camera, a position and/or orientation of the image projector may be computed relative to a position and/or orientation of the depth camera. As a non-limiting example, the POSIT (Pose from Orthography and Scaling with Iterations) algorithm may be used to compute the relative position and/or orientation of image projector. However, it will be understood that other suitable techniques may be applied.

When included, communication subsystem 1022 may be configured to communicatively couple computing system 1010 with one or more other computing devices. Communication subsystem 1022 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing system 1010 to send and/or receive messages to and/or from other devices via a network such as the Internet. Peripheral devices may be operatively connected to logic subsystem 1012 and/or storage subsystem 1014 as well as other components of computing system 1010 via communication subsystem 1022 using any suitable technology. Non-limiting examples include wired technologies such as HDMI, universal serial bus, etc. and/or wireless technologies such as Wi-Fi, Bluetooth, etc.

FIG. 10 shows further aspects of storage subsystem 1014 including a non-limiting example of instructions 1030. Instructions 1030 may include or define an operating system 1032. Operating system 1032 may include an API 1034. Instructions 1030 further include application program 1036. Operating system 1032 may be configured to receive one or more API calls from application program 1036 via API 1034. Responsive to an API call, operating system 1032 may be configured to perform a function and/or send one or more API responses to application program 1036 or a different application program via API 1034.

Non-limiting examples of API calls that may be supported by operating system 1032 may be used by an application program to indicate: an identity (e.g., left-hand, right-hand, left-foot, right-foot, etc.) of a body portion to be tracked; an identity of a body portion onto which a visual cue is to be projected; whether the visual cue is to be projected onto the human subject or into a field of view of the human subject; a type (e.g., directional indicator, color, model path of travel) of the visual cue projected onto the human subject or into a field of view of the human subject; a definition of the model path of travel; whether the visual cue is to provide feedback information and/or feedforward information; and/or the type of approach to be used to guide the human subject toward the model path of travel (e.g., absolute, relaxed absolute, or relative). It will be understood that other suitable API calls may be supported by operating system 1032, including API calls that define other aspects of the functionality described herein.

Movement of a human subject or a body portion of a human subject that is imaged by one or more optical sensors may be used provide a control input to an electronic device. For example, the control input may be used to manipulate application program 1036 and/or operating system 1032. As a non-limiting example, instructions 1030 may provide or otherwise support a processing pipeline in which a human subject is modeled. It will be appreciated that a processing pipeline may include additional steps and/or alternative steps than those described herein without departing from the scope of this disclosure. A three-dimensional appearance of a human subject and the rest of an observed scene may be imaged by a depth camera. The depth camera may determine, for each pixel, the three dimensional depth of a surface in the observed scene relative to the depth camera.

The three dimensional depth information determined for each pixel may be used to generate a depth map. A depth map may take the form of virtually any suitable data structure, including but not limited to a matrix that includes a depth value for each pixel of the observed scene. It is to be understood that a depth map may include depth information for all pixels, not just pixels that image a human subject.

A virtual skeleton may be derived from the depth map to provide a machine-readable representation of the human subject. In other words, the virtual skeleton may be derived from the depth map to model the human subject. The virtual skeleton may be derived from the depth map in any suitable manner. In some embodiments, one or more skeletal fitting algorithms may be applied to the depth map. The present disclosure is compatible with virtually any skeletal modeling technique.

The virtual skeleton may include a plurality of joints, and each joint may correspond to a portion of the human subject. Virtual skeletons in accordance with the present disclosure may include virtually any number of joints, each of which can be associated with virtually any number of parameters (e.g., three dimensional joint position, joint rotation, body posture of corresponding body part (e.g., hand open, hand closed, etc.) etc.). It is to be understood that a virtual skeleton may take the form of a data structure including one or more parameters for each of a plurality of skeletal joints (e.g., a joint matrix including an x position, a y position, a z position, and a rotation for each joint). In some embodiments, other types of virtual skeletons may be used (e.g., a wireframe, a set of shape primitives, etc.).

In the context of a hand of a human subject, for example, a hand joint of the virtual skeleton may be identified, and the portion of the depth map corresponding to the hand joint may be analyzed to determine a position and posture of the users hand.

In at least some implementations, the shape of the visual cue may be augmented before it is projected onto a physical object to accommodate the surface geometry of that physical object as identified from the depth map. For example, an original visual cue may be processed by logic subsystem 1012 executing instructions 1030 prior to projecting the processed visual cue onto a target surface so that the visual cue when viewed by the human subject at the target surface appears as the original visual cue. It will be understood that any suitable technique may be applied to process the visual cue prior to projecting that visual cue.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of guiding physical movement of a human subject, the method comprising:

observing, via one or more cameras, a physical environment;

identifying, with a computing device configured to process image data from the camera, a current three-dimensional position of a body portion of a human subject within the physical environment;

obtaining, with the computing device, a model path of future travel for the body portion of the human subject; and projecting, via an image projector, a visual cue onto the human subject at the current three-dimensional position of the body portion, the visual cue indicating the model path of future travel for the body portion of the human subject.

2. The method of claim 1, wherein the visual cue further indicates how the human subject's previous physical movements tracked a model path of travel.

3. The method of claim 1, wherein the visual cue indicates the model path of future travel by showing how the human subject's future physical movements can mimic the model path of travel.

4. The method of claim 1, wherein the visual cue indicates the model path of future travel by showing a deviation between the current position of the body portion and a model position along the model path of future travel.

5. The method of claim 4, further comprising:
determining one or both of a magnitude and a direction of the deviation between the current position of the body portion and the model position along the model path of future travel;
wherein the visual cue indicates one or both of the magnitude and the direction of the deviation.

6. The method of claim 1, wherein projecting the visual cue onto the human subject includes projecting the visual cue onto the body portion of the human subject.

7. The method of claim 1, wherein the model path of future travel is a multi-dimensional model path of travel.

8. The method of claim 1, wherein the visual cue includes a visual representation of a multi-dimensional directional indicator.

9. The method of claim 1, wherein the visual cue includes a directional indicator that guides the body portion of the human subject toward or along the model path of future travel.

10. The method of claim 1, wherein the visual cue includes one or more colors that indicate the current position of the body portion relative to the model path of future travel.

11. The method of claim 1, wherein the visual cue directs the body portion of the human subject toward the model path of future travel by:
directing the body portion toward a future model position of the model path of travel; or
directing the body portion along a parallel model path of travel offset from the model path of future travel.

12. The method of claim 1, wherein the visual cue indicates the model path of future travel by following the model path of future travel.

13. The method of claim 1 further comprising:
updating the current position of the body portion of the human subject over time as the body portion moves within the physical environment; and
varying a spatial parameter of projection of the visual cue as the body portion moves within the physical environment to maintain projection of the visual cue within a boundary of the body portion.

14. A computer comprising:
a depth-camera input to receive depth-camera information from a depth camera;
an image-projector output to send projector information to an image projector;
a processor operatively connected to the depth-camera input and to the image-projector output;
a storage device holding instructions executable by the processor to:
identify, from the depth-camera information, a current three-dimensional position of a body portion of a human subject imaged by the depth camera;
obtain a model path of future travel for the body portion of the human subject; and
project a visual cue via the image projector onto the human subject at the current three-dimensional position, the visual cue indicating the model path of future travel for the body portion of the human subject.

15. The storage device of claim 14, wherein the visual cue further indicates how the human subject's previous physical movements tracked the model path of travel.

16. The storage device of claim 14, wherein the visual cue indicates the model path of future travel by showing how the human subject's future physical movements can mimic the model path of future travel.

17. The storage device of claim 14, wherein the visual cue includes a visual representation of the model path of future travel.

18. The storage device of claim 14, wherein the visual cue includes one or more of a directional indicator indicating a deviation between the current position of the body portion and a model position along the model path of future travel.

19. The storage device of claim 14, wherein the visual cue includes one or more colors indicating a deviation between the current position of the body portion and a model position along the model path of future travel.

20. A method of guiding physical movement of a human subject, the method comprising:
identifying, with a computing device configured to process image data from a camera, a current three-dimensional position of a body portion of a human subject within a physical environment;
obtaining a multi-dimensional model path of future travel for the body portion of the human subject; and
projecting a visual cue onto the body portion at the current three-dimensional position via one or more image projectors, the visual cue including:
a visible light portion that indicates a first direction of movement for the body portion toward or along the model path of future travel in a first plane, and
a directional indicator that indicates a second direction of movement for the body portion toward or along the model path of future travel perpendicular to the first plane.

* * * * *